United States Patent [19]

Horn et al.

[11] Patent Number: 4,522,743

[45] Date of Patent: Jun. 11, 1985

[54] PREPARATION OF FINELY DIVIDED PULVERULENT CAROTINOID AND RETINOID COMPOSITIONS

[75] Inventors: Dieter Horn, Heidelberg; Hans W. Schmidt, Mannheim; Walter Ditter, Heidelberg; Horst Hartmann, Boehl-Iggelheim; Erik Lueddecke, Mutterstadt; Klaus Schmieder, Frankenthal, all of Fed. Rep. of Germany

[73] Assignee: BASF Aktiengesellschaft, Fed. Rep. of Germany

[21] Appl. No.: 376,585

[22] Filed: May 10, 1982

[30] Foreign Application Priority Data

May 15, 1981 [DE] Fed. Rep. of Germany ....... 3119383

[51] Int. Cl.³ .............................................. B01J 13/00
[52] U.S. Cl. .................................... 252/311; 252/306; 252/312; 426/73; 426/540
[58] Field of Search .................... 252/306, 311, 312; 426/73, 540; 424/341

[56] References Cited

U.S. PATENT DOCUMENTS

| 2,650,895 | 9/1953 | Wallenmeyer et al. | 167/81 |
| 3,110,598 | 11/1963 | Müller | 426/540 |
| 3,655,406 | 4/1972 | Klaui | 426/540 |
| 3,734,745 | 5/1973 | Cassanelli et al. | 426/540 |
| 3,790,688 | 2/1974 | Walter et al. | 426/540 |
| 4,316,917 | 2/1982 | Antoshkiw et al. | 426/73 |

FOREIGN PATENT DOCUMENTS

| 1211911 | 3/1966 | Fed. Rep. of Germany . |
| 2534091 | 2/1976 | Fed. Rep. of Germany . |
| 304023 | 3/1955 | Switzerland . |

OTHER PUBLICATIONS

Chemical Abstracts, vol. 83, No. 11, (1975), p. 414, No. 176994e.

Primary Examiner—Richard D. Lovering
Assistant Examiner—Anne Brookes
Attorney, Agent, or Firm—Keil & Weinkauf

[57] ABSTRACT

Finely divided, pulverulent carotinoid or retinoid compositions, in which the carotinoid or retinoid essentially has a particle size of less than 0.5 micron, are prepared by a process wherein a carotinoid or retinoid is dissolved in a volatile, water-miscible, organic solvent at from 50° C. to 200° C., if necessary under superatmospheric pressure, within the space of less than 10 seconds. The carotinoid is immediately precipitated, in a colloidally disperse form, from the molecularly disperse solution by rapidly mixing the latter with an aqueous solution of a swellable colloid at from 0° C. to 50° C., and the resulting dispersion is freed from the solvent and the dispersing medium in a conventional manner.

5 Claims, 1 Drawing Figure

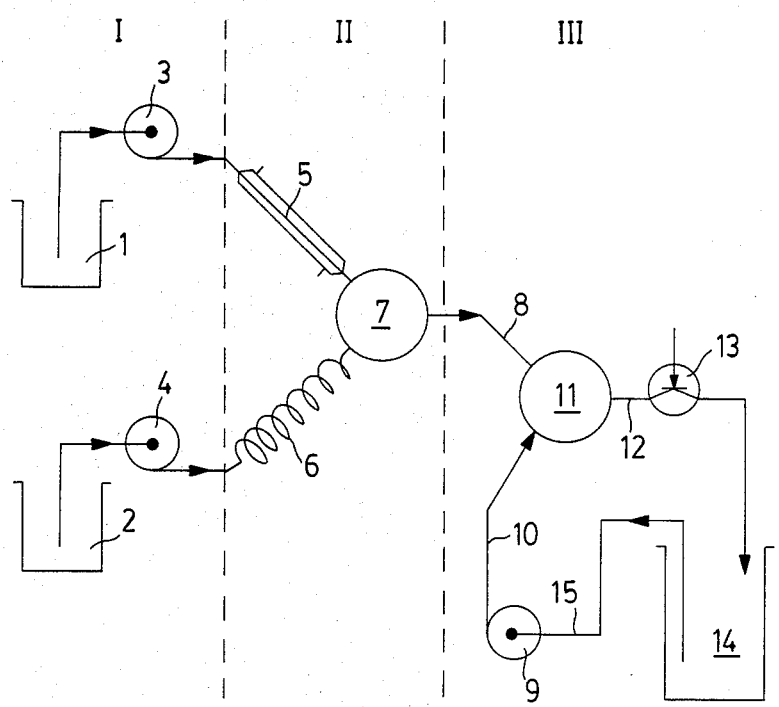

PREPARATION OF FINELY DIVIDED PULVERULENT CAROTINOID AND RETINOID COMPOSITIONS

The present invention relates to a process for converting carotinoids and retinoids into a finely divided pulverulent form which is in particular required for coloring foodstuffs and animal feeds.

The carotinoids are a group of colored pigments which have a yellow to red hue, are widely found in nature, and impart a characteristic color to many foodstuffs. The most important examples of this category include $\beta$-carotene, $\beta$-apo-8'-carotinal, canthaxanthin and citranaxanthin. In the foodstuff and animal feed industries, and in pharmaceutical technology, these substances, which can be prepared synthetically, are important colorants, for example as substitutes for artificial dyes, or are of interest because of, for example, their pro-vitamin A activity.

All carotinoids are water-insoluble, and only slightly soluble in fats and oils. This limited solubility, and high sensitivity to oxidation, prevent direct use of the relatively coarse products, obtained from synthesis, for coloring foodstuffs or animal feeds, since only low color yields are attainable and in a coarsely crystalline form the substances are poorly absorbed by the organism. These adverse effects in respect of the practical use of the carotinoids are especially pronounced in aqueous media, in which the carotinoids are completely insoluble.

To improve the color yields and increase the absorption in the organism, various processes have been described, all with the common object of reducing the crystallite size of the active ingredients to a range of less than 10 $\mu$m. For example, according to Chimia 21 (1967), 329, $\beta$-carotene can be milled with edible oil under nitrogen in a colloid mill to a particle size of from 2 to 5 $\mu$m. According to Food Technol. 12 (1958), 527 the surrounding oil at the same time protects the active ingredient against oxidation. A suspension thus obtained and containing up to 20 to 30% of active ingredient can be used successfully for coloring fats and oils since the solubility, though low, suffices to bring the crystals into solution at the low concentration conventionally employed.

However, compounding the active ingredients for use in an aqueous medium proves far more difficult. In an aqueous medium, the carotinoids show no detectable solubility and the desired color characteristics and absorption by the organism can only be achieved through an extremely finely divided crystalline state. For this, a particle size of less than 1 $\mu$m is desirable, and milling is either entirely unable to provide this or can only do so with damage to the active ingredient. Attempts first to dissolve the carotinoids, using a water-soluble organic solubilizing agent, such as alcohol or acetone, and then to precipitate them in a finely crystalline form by dilution with water, have hitherto failed due to the inadequate solubility of the carotinoids in these solvents. For example, the solubility of $\beta$-carotene at room temperature is less than 0.1% by weight in acetone and less than 0.01% by weight in ethanol.

Other processes for the preparation of a composition in which the active ingredients are finely divided entail applying these ingredients to carriers, such as starch, pectin or dried milk powder; for example, in German Pat. No. 642,307 a solution of the active ingredient in oil, and in German Pat. No. 861,637 and Swiss Pat. No. 304,023 a solution of the active ingredient in chloroform, is sprayed onto the carrier. However, the compositions obtained are not universally dispersible in aqueous media and do not conform to the conventional shelf life requirements, since the active ingredients deposited on the surface rapidly undergo oxidative degradation. Finally, there are processes in which active ingredients in the form of solutions in oil are embedded in an emulsion-like manner in colloids such as gelatin, as described in Chimia 21 (1967), 329, French Pat. No. 1,056,114 and U.S. Pat. No. 2,650,895. However, the concentration of active ingredient in such a composition is low, because of the low solubility of the ingredient in oil.

Some improvement over these methods is provided by prior art processes in which the active ingredient is emulsified in a water-immiscible solvent, preferably a hydrocarbon, eg. chloroform or methylene chloride, the solution is emulsified in a gelatin/sugar solution by homogenization, and finally the solvent is stripped from the emulsion, liberating the active ingredient in a finely crystalline form. This process is described in Chimia 21 (1967), 329, German Published Application DAS No. 1,211,911 and German Laid-Open Application DOS No. 2,534,091. The suspension obtained is finally converted to a finely divided powder by dehydration.

However, this process has the disadvantage that chlorohydrocarbons must be used to give a sufficiently high concentration of active ingredient in the emulsion phase, and complete removal—essential for toxicological reasons—of the chlorohydrocarbons is industrially difficult to attain.

It is an object of the present invention to provide a process which does not suffer from the above disadvantages and which permits the preparation of very finely divided free-flowing powders of carotinoids.

We have found that this object is achieved, according to the invention, by a process for the preparation of finely divided, pulverulent carotinoid compositions, especially for coloring foodstuffs and animal feeds, wherein a carotinoid is dissolved in a volatile, water-miscible, organic solvent at from 50° C. to 200° C., preferably from 100° C. to 180° C., if necessary under superatmospheric pressure, within the space of less than 10 seconds, the carotinoid is immediately precipitated, in a colloidally disperse form, from the molecularly disperse solution by rapidly mixing the latter with an aqueous solution of a swellable colloid at from 0° C. to 50° C., and the resulting dispersion is freed from the solvent and the dispersing medium in a conventional manner.

Though the invention is preferably applied to the preparation of carotinoid compositions, we have found that retinoids can similarly be converted to a finely divided form.

Retinoids, for the purpose of the present invention, in particular include all-trans-retinoic acid, 13-cis-retinoic acid and the esters and amides of these acids. The formulae of these retinoids are given in detail by D. L. Newton, W. R. Henderson and M. B. Sporn in Cancer Research 40, 3413–3425, which publication is hereby incorporated by reference.

The process according to the invention makes use of the fact that the solubility of carotinoids in water-miscible solvents, which is very low when the solvents are cold, substantially increases with increasing temperature. However, there existed a considerable prejudice against heating carotinoids, since such heating as a rule leads to partial decomposition and to isomerization of the compounds, affecting the hue.

The carotinoids which can be employed in carrying out the invention are the conventional accessible natural or synthetic members of this class of compounds, which are useful as colorants, eg. carotene, lycopin, bixin, zeaxanthin, cryptoxanthin, citranaxanthin, lutein, canthaxanthin, astaxanthin, $\beta$-apo-4'-carotinal, $\beta$-apo-8'-carotinal, $\beta$-apo-12'-carotinal, $\beta$-apo-8'-carotinic acid and esters of hydroxy-containing and carboxy-containing members of this group, for example the lower alkyl esters, preferably the methyl and ethyl esters. Preferred compounds are those which have hitherto been readily obtainable industrially, eg. $\beta$-carotene, canthaxanthin, $\beta$-apo-8'-carotinal and $\beta$-apo-8'-carotinic acid esters.

Suitable solvents for carrying out the process according to the invention are, in particular, water-miscible thermally stable volatile solvents containing only carbon, hydrogen and oxygen, eg. alcohols, ethers, esters, ketones and acetals. Preferably, ethanol, n-propanol, isopropanol, butane-1,2-diol 1-methyl ether, propane-1,2-diol 1-n-propyl ether or acetone is used.

In general, it is advantageous to use solvents which are water-miscible to the extent of at least 10%, have a boiling point below 200° C. and/or are of less than 10 carbon atoms.

Examples of swellable colloids used are gelatin, starch, dextrin, pectin, gum arabic, casein, caseinate and mixtures of these. However, polyvinyl alcohol, polyvinylpyrrolidone, methylcellulose, carboxymethylcellulose, hydroxypropylcellulose and alginates may also be employed. For further details, reference may be made to R. A. Morton, Fat Soluble Vitamins, Intern. Encyclopedia of Food and Nutrition, Volume 9, Pergamon Press 1970, pages 128-131. To increase the mechanical stability of the end product, it is advantageous to add to the colloid a plasticizer such as a sugar or sugar alcohol, eg. sucrose, glucose, lactose, invert sugar, sorbitol, mannitol or glycerol.

The ratio of colloid and plasticizer to carotinoid solution is in general so chosen that the end product obtained contains from 0.5 to 20% by weight, preferably about 10% by weight of carotinoid or retinoid, from 10 to 50% by weight of a swellable colloid and from 20 to 70% by weight of a plasticizer, all percentages being based on the dry weight of the powder, with or without minor amounts of a stabilizer; the mean particle size of the carotinoid or retinoid in the powder is less than 0.3 $\mu$m and the half-width of the particle size distribution is less than 50%, with virtually no material of particle size greater than 1 $\mu$m.

To increase the stability of the active ingredient to oxidative degradation, it is advantageous to add stabilizers, eg. $\alpha$-tocopherol, t-butyl-hydroxy-toluene, t-butylhydroxyanisole or ethoxyquine. They can be added either to the aqueous phase or to the solvent phase, but are preferably dissolved, conjointly with the colorants and surfactant stabilizers, in the solvent phase. Under certain circumstances it may be advantageous additionally to dissolve an oil or fat in the solvent phase; this material is then precipitated, conjointly with the active ingredients and the said additives, in an extremely finely divided form when the solution is mixed with the aqueous phase.

The active ingredient concentration in the dispersion obtained after precipitation of the carotinoids can be increased by flocculating the colloidally disperse system, either by addition of salt or by bringing it to a suitable pH, and the dispersion can thereby be converted to a form from which a part of the dispersion medium can be separated off in a simple manner, by filtering or centrifuging, the finely divided carotinoids remaining in the liquid phase. When using a mixture of gelatin and gum arabic as the swellable colloid, the formation—controllable through the pH—of a filtrable or sedimentable coacervate can be utilized particularly advantageously to increase the solids concentration in the dispersion.

The product obtained is a deeply colored viscous liquid, whose properties depend on the nature and amount of the colloid used and which, in the case of a gellable colloid, solidifies to a gel. The solvent can be removed in a conventional manner, depending on its boiling point, for example by distillation, if appropriate under reduced pressure, or by extraction with a water-immiscible solvent. In the latter case it has proved feasible and advantageous, when using isopropanol, to employ the azeotrope formed directly as the solvent without removal of water. Preferably, however, the extraction is effected conjointly with removal of water by spray drying or spray granulation.

A dry powder is obtained which, when using a water-soluble colloid, can be redissolved in water to give uniform fine dispersion of the active ingredient as particles < 1 $\mu$m in size. In a photochemical stability test, the active ingredient hydrosol thus obtained proves extremely stable, notwithstanding the fineness of dispersion.

Reference is now made to the accompanying drawing where an apparatus suitable for carrying out the process in accordance with the instant invention is diagrammatically illustrated in FIG. 1.

As seen, FIG. 1 shows an apparatus with three sections designated I, II and III, respectively. Sections I and III represent those areas of the apparatus wherein operations are conducted at relatively low temperatures while section II represents a high temperature zone. The parts of the various sections as shown in the drawing are described in the following discussion on the use of the illustrated apparatus in carrying out the process.

A suspension of the carotinoid in the selected solvent, at a concentration of from 2 to 40% by weight based on the mixture, with or without addition of from 0.1 to 10% by weight of stabilizers, is initially introduced into the vessel (1). The vessel (2) contains the solvent, without admixed carotinoid. The active ingredient suspension and the solvent are fed to the mixing chamber (7) via the pumps (3) and (4) respectively, the mixing ratio being predeterminable by choice of the delivery rate of each pump. The ratio is selected to be such as to give—depending on the solvent used and on the residence time—a carotinoid concentration of from 0.5 to 10% by weight, based on the solution, in the mixing chamber. The volume of the mixing chamber (7) is such that at the chosen delivery rate of the pumps (3) and (4) the residence time in (7) is preferably less than 1 second.

Before it enters the mixing chamber, the solvent is brought to the desired temperature by means of the heat exchanger (6), while the active ingredient suspension is kept at below 50° C. by feeding it to the chamber via the thermally insulated line (5). As a result of turbulent mixing in (7), dissolution of the active ingredient occurs at from 50° to 200° C., especially from 100° to 180° C., preferably from 140° to 180° C., and the solution obtained passes, after a short residence time of preferably less than one second, via (8) into the second mixing chamber (11), where the active ingredient is precipitated in a colloidally disperse form by admixture of water or of an aqueous protective colloid solution via the pump (9) and the feed line (10). The finely divided active ingredient dispersion is then discharged via the line (12) and pressure-relief valve (13) and is led to the stock vessel (14). To achieve the highest possible concentration of active ingredient, the dispersion can be recycled via the suction line (15).

If the pressure-relief valve (13) is set to pressures greater than 1 bar, the novel process can even be carried out with solvents above their boiling point (at atmospheric pressure).

A pulverulent composition can be isolated from the dispersion by conventional methods, for example as described in German Laid-Open Application DOS No. 2,534,091 by spray drying or by spray cooling or by encapsulating the particles, separating them off and drying the product in a fluidized bed.

For spray drying, either the dispersion is first freed from solvent by distillation, preferably under reduced pressure, or by extraction with a water-immiscible solvent, or the entire mixture is spray-dried and water and solvent are thus stripped off jointly in the spraying tower.

At the bottom of the spraying tower, the carotinoid powder is obtained either dry or at least free-flowing. In some cases it may be advantageous to effect final drying by an additional step in a fluidized bed.

Instead of preparing the powder by spray drying, any other suitable method for converting the carotinoid, present in a finely divided form in the water/solvent dispersion, to a powder may be used.

An example of a conventional process which is equally suitable for the present purpose is to emulsify the dispersion, which has been freed from solvent, with paraffin oil, cool the mixture, separate the paraffin oil from the encapsulated carotinoid particles, wash the resulting carotinoid composition with gasoline and dry the product in a fluidized bed.

Particularly surprising features of the procedure according to the invention are that, using the above water-miscible solvents at an elevated temperature, the rate of dissolution suffices, in spite of the low contact time of less than 1 second, to give molecularly disperse solutions containing from 0.5 to 10% of the active ingredients—a result hitherto only achievable with halohydrocarbons—and that in spite of the high temperature the rate of isomerization is insufficient to produce a detectable increase in cis-isomer concentration within the short residence time in solution form.

A further surprising feature is that on mixing the carotinoid solution, which may additionally contain stabilizers such as ascorbyl palmitate, monoglycerides, diglycerides, esters of monoglycerides with acetic acid, citric acid, lactic acid or diacetyltartaric acid, polyglycerol fatty acid esters, sorbitan fatty acid esters, propylene glycol fatty acid esters, stearyl-2-lactylates or lecithin, with the aqueous solution of the swellable colloids an extremely finely divided and nevertheless very stable carotinoid composition is obtained, in which moreover the degree of fineness may be controlled through the choice of the stabilizers added to the carotinoid solution. This finely divided state of the active ingredient persists even during removal of the volatile solvent, for example by spray drying. It is readily possible to obtain compositions in which the greater part of the active ingredient is present as particles of size about 0.2 μm, without the simultaneous presence of active ingredient particles larger than 1 μm.

The Examples which follow illustrate the process according to the invention.

EXAMPLE 1

5 g of β-trans-carotene are suspended in 80 g of a solution of 0.8 g of dl-α-tocopherol and 0.8 g of ascorbyl palmitate in butane-1,2-diol 1-methyl ether at 25° C. and this suspension is mixed, at 135°–140° C., with 100 g of butane-1,2-diol 1-methyl ether (boiling point 138° C.) in the mixing chamber (7) (FIG. 1), allowing a residence time of 0.3 second. The resulting molecularly disperse solution is immediately afterwards fed via the line (8) to the mixing chamber (11) in which the β-carotene is precipitated in a colloidally disperse form by mixing with 800 g of an aqueous gelatin solution which has been brought to pH 9.5 with 1N NaOH and which in addition to 13.2 g of gelatin contains 6 g of dextrose and 3.6 g of dextrin. The entire process is carried out with the pressure-relief valve (13) set to 5 bar, in order to avoid evaporation of the solvent during the process of fine dispersion.

In the collecting vessel (14), a colloidally disperse β-carotene dispersion having an orange-yellow hue is obtained.

The particle size of the β-carotene is found to be 0.25 μm, with a distribution width of ±50%, by laser photon correlation spectroscopy as described by B. Chu, Laser Light Scattering; Academic Press, New York 1974.

Spectroscopic analysis of the β-carotene by the method of FAO Nutrition Meetings Report Series No. 54 B, WHO/Food Add./7 18th Report, 1974, at wavelengths of 455 and 340 nm, gives an extinction ratio of $E_{455}/E_{340} = 15.3$, thus conforming to the specification for all-trans-β-carotene.

Spray drying of the dispersion gives a free-flowing dry powder which dissolves in water to form a clear yellowish dispersion.

EXAMPLE 2

A molecularly disperse solution of 5 g of trans-β-carotene in butane-1,2-diol 1-methyl ether is prepared in the mixing chamber as described in Example 1, and is immediately thereafter fed to the mixing chamber (11), in which the β-carotene is precipitated in a colloidally disperse form by mixing with 800 g of an aqueous solution, brought to pH 9.5 with 1N NaOH, of 7.9 g of gelatin and 5.3 g of gum arabic as well as 6 g of dextrose and 3.6 g of dextrin. The pH of the orange-yellow dispersion is then brought to pH 4–4.5 with 1N sulfuric acid and the solid constituent of the dispersion is thereby flocculated. On separating off the liquid phase and repeated washing, a product is obtained which is free from residual solvent and can be converted to a dry powder by spray drying or spray granulation.

EXAMPLE 3

Using the method described in Example 1, but with acetone as the solvent and with the pressure-relief valve (13) set to 25 bar, 5 g of trans-β-carotene together with 0.8 g of dl-α-tocopherol and 0.8 g of ascorbyl palmitate are suspended in 85 g of acetone and the suspension is mixed continuously with 130 g of acetone in the mixing chamber (7). With a dosage rate of 2 l/h on the suspension side and 3 l/h on the solvent side the residence time in the mixing cell is 0.35 second. The molecularly disperse solution is then mixed, in mixing chamber (11), with an aqueous solution, brought to pH 9.5, of 13.2 g of gelatin, 5.9 g of dextrose, 1.8 g of dextrin and 1.8 g of a diacetyl-tartaric acid ester of a fatty acid monoglyceride, at a throughput of 45 l/h. A colloidally disperse active ingredient suspension having an orange-yellow hue is obtained. Particle size analysis shows a mean value of 0.27 μm, with a distribution width of ±46%. Spectroscopic analysis gives a to-specification extinction ratio of $E_{455}/E_{340} = 15.2$.

After removing the solvent under reduced pressure at 50° C. in a distillation apparatus, a colloidally disperse active ingredient dispersion is obtained, which can be converted, by spray drying, to a stable, readily water-soluble dry powder.

EXAMPLES 4–6

Using the method described in Example 3, the water-dispersible, spray-dried β-carotene powders listed in Table I are obtained; they have the compositions shown, and contain 4%, 6% and 10% of β-carotene.

TABLE I

|  |  | 4% | 6% | 10% |
|---|---|---|---|---|
| β-carotene | solvent phase | 1 g | 1.5 g | 2.7 g |
| dl-α-tocopherol |  | 0.8 g | 0.8 g | 0.8 g |
| ascorbyl palmitate |  | 0.8 g | 0.8 g | 0.8 g |
| dextrose | aqueous phase | 5.9 g | 5.9 g | 5.9 g |
| dextrin |  | 1.8 g | 1.8 g | 1.8 g |
| citric acid ester of a fatty acid monoglyceride |  | 1.8 g | 1.8 g | 1.8 g |
| gelatin |  | 13.2 g | 13.2 g | 13.2 g |

EXAMPLES 7–9

Using the method described in Example 3, dry powders of the compositions shown in Table II are prepared from the carotinoids canthaxanthin, citranaxanthin and ethyl β-apo-8'-carotinate; each of these powders contains 11.6% of the carotinoid.

TABLE II

|  |  | Example 1 | Example 8 | Example 9 |
|---|---|---|---|---|
| carotinoid | solvent phase | 5 g of canthaxathin | 5 g of citranaxanthin | 5 g of ethyl β-apo-8'-carotinate |
| dl-α-tocopherol |  | 0.8 g | 0.8 g | 0.8 g |
| ascorbyl palmitate |  | 0.8 g | 0.8 g | 0.8 g |
| dextrose | aqueous phase | 5.9 g | 5.9 g | 5.9 g |
| dextrin |  | 3.6 g | 3.6 g | 3.6 g |
| gelatin |  | 27.1 g | 27.1 g | 27.1 g |
| particle size |  | 0.15 ± 30% μm | 0.19 ± 37% μm | 0.23 ± 40% μm |

EXAMPLES 10–13

Dry powders are prepared from the carotinoids β-carotene, canthaxanthin, citranaxanthin and ethyl β-apo-8'-carotinate as described in Examples 7 to 9, but using ethanol as the solvent. The size distribution of the carotinoid particles in the compositions is listed in Table III.

TABLE III

| Carotinoid | Mean particle size | Distribution width |
|---|---|---|
| β-carotene | 0.18 μm | ±42% |
| canthaxanthin | 0.14 μm | ±27% |
| citranaxanthin | 0.16 μm | ±16% |
| ethyl β-apo-8'-carotinate | 0.18 μm | ±22% |

EXAMPLE 14

30 g of canthaxanthin together with 1.1 g of ascorbyl palmitate and 6.4 g of ethoxyquine are suspended in 240 g of isopropanol and the suspension is mixed continuously with 370 g of isopropanol in the mixing chamber (7), with the pressure-relief valve (13) set to 30 bar. At a dosage rate of 6 l/h on the suspension side and 9 l/h on the solvent side, a mixing temperature of 173° C. is obtained in the mixing chamber (7). After a residence time of 0.3 second, the molecularly disperse solution in the mixing chamber (11) is mixed with a solution, brought to pH 9.5, of 38.6 g of gelatin and 105 g of dextrose in 4,000 g of water at a throughput of 80 l/h of isobutanol. A colloidally disperse active ingredient suspension having a red hue is obtained. Particle size analysis shows a mean value of 0.15 μm, with a distribution width of ±31%.

After separating off the solvent under reduced pressure in a distillation apparatus, an active ingredient dispersion is obtained which can be converted to a stable, water-soluble dry powder by spray drying. Measurements on a solution of this powder in water show a particle size of 0.17 μm ± 30%.

EXAMPLE 15

Canthaxanthin can be finely dispersed, similarly to Example 14, by using an isopropanol/water azeotrope containing 12% by weight of water. The active ingredient suspension obtained has a mean particle size of 0.16 μm ± 35%.

EXAMPLE 16

5 g of 13-Z-vitamin A-acid are suspended in 40 g of isopropanol and mixed continuously, at a dosage rate of 3 l/h, with 46 g of isopropanol, at a dosage rate of 4.5 l/h, in mixing chamber (7). The steady-state mixing temperature is 172° C. Immediately thereafter, the active ingredient is precipitated continuously, in mixing chamber (11), by turbulent mixing with a solution, brought to pH 3.0, of 10 g of gelatin and 25 g of dextrose in 1,000 g of water, at a dosage rate of 80 l/h. A colloidally disperse active ingredient suspension having a yellow hue is obtained. The particle size is 0.23 μm ± 25%. After separating off the solvent, spray drying yields a water-soluble dry powder.

EXAMPLE 17

The procedure described in Example 15 is followed, except that N-4-hydroxyphenylretinamide is used as the active ingredient and a mixture of 50% by weight of isopropanol and 50% by weight of water as the suspension medium for the active ingredient and as the solvent. 5 g of the retinoid are dissolved continuously in the mixing chamber (7) at a mixing temperature of 150° C., the solution is mixed continuously, in mixing chamber (11), with 1,240 g of an aqueous solution containing 12 g of gelatin and 33 g of dextrose, and the retinoid is thereby converted to a finely disperse form. Measurement of the particle size distribution gives a mean value of 0.23 μm, with a distribution width of ±44%. After stripping off the solvent, the finely divided product is converted to a water-soluble dry powder by spray drying.

We claim:

1. A process for the preparation of finely divided, pulverulent carotinoid or retinoid compositions, in which the carotinoid or retinoid essentially has a particle size of less than 0.5 micron, wherein a carotinoid or retinoid is dissolved in a volatile, water-miscible, organic solvent at from 100° C. to 200° C., if necessary under superatmospheric pressure, within the space of less than 10 seconds, the carotinoid or the retinoid is immediately precipitated, in a colloidally disperse form, from the molecularly disperse solution by rapidly mixing the latter with an aqueous solution of a swellable colloid at from 0° C. to 50° C., and the resulting dispersion is freed from the solvent and the dispersing medium in a conventional manner.

2. A process for the preparation of a finely divided, pulverulent carotinoid or retinoid composition as claimed in claim 1, wherein the water-miscible volatile solvent used is an alcohol, ketone, ester, acetal or ether.

3. A process for the preparation of a carotinoid or retinoid composition as claimed in claim 2, wherein the water-miscible volatile solvent used is acetone, butane-1,2-diol 1-methyl ether, propane-1,2-diol 1-n-propyl ether, ethanol, n-propanol, isopropanol or mixtures of these.

4. A process as claimed in claim 1, wherein the preparation of the molecularly disperse carotinoid or retinoid solution and the precipitation of the carotinoid or retinoid in a very finely disperse form are effected continuously in two mixing chambers connected in series.

5. A pulverulent carotinoid or retinoid composition prepared by a process as claimed in claim 1 and containing from 0.5 to 20% by weight of a carotinoid or retinoid, from 10 to 50% by weight of a swellable colloid and from 20 to 70% by weight of a plasticizer, all percentages being based on the dry weight of the powder, with or without minor amounts of a stabilizer, wherein the mean particle size of the carotinoid or retinoid is less than 0.3 μm and the half-width of the particle size distribution is less than 50%, with virtually no material of particle size greater than 1 μm.

* * * * *